United States Patent [19]

Evangelista et al.

[11] Patent Number: 5,363,690
[45] Date of Patent: Nov. 15, 1994

[54] GAS DETECTION APPARATUS

[75] Inventors: Richard A. Evangelista, Downingtown; Stephen D. Summerfield, Philadelphia; Leslie S. Cerovich, King of Prussia, all of Pa.

[73] Assignee: Exidyne Instrumentation Technologies, Inc., Exton, Pa.

[21] Appl. No.: 953,892

[22] Filed: Sep. 30, 1992
(Under 37 CFR 1.47)

[51] Int. Cl.$^5$ ............................................. G01N 27/00
[52] U.S. Cl. .................................. 73/31.05; 73/31.02
[58] Field of Search ................ 73/31.05, 31.03, 31.01, 73/31.02

[56] References Cited

U.S. PATENT DOCUMENTS 3,415,108  12/1968  Hübner ............................... 73/31.05
3,427,862   2/1969  Hübner ........................... 73/31.05 X

OTHER PUBLICATIONS

Copy of promotional sheet on EIT's Combustible Gas Transmitter Model No. 4388.
Copy of promotional sheet on EIT's Dual Gas Detector Model No. 5102.
*New Sensor Stik Transmitter* EIT Monitor vol. 1, No. 2, Jul. 1991.

*Primary Examiner*—Hezron E. Williams
*Assistant Examiner*—Joseph W. Roskos
*Attorney, Agent, or Firm*—Samuels, Gauthier & Stevens

[57] ABSTRACT

A gas detection apparatus having a microprocessor control circuit mounted within a housing chamber which is operable for processing input signals associated with measured gas levels and generating output signals corresponding to same to the output port. An interchangeable electrochemical sensor device is removably disposed within the chamber via an access opening of the housing, the sensor being operable for sensing and measuring gas levels and generating the input signals to the microprocessor circuit. An elastomeric connector unit is removably and sealingly disposed between interfacing contact surfaces of the sensor and control circuit via the access opening. The connector unit provides a conductive path between the microprocessor circuit and the sensor device and electromagnetic shielding therebetween.

10 Claims, 4 Drawing Sheets

5,363,690

GAS DETECTION APPARATUS

BACKGROUND OF THE INVENTION

The invention relates to gas sensing devices, and in particular to apparatus which detect the presence of toxic gas in the air and which emits a signal being linearly proportional to the toxic gas concentration in the surrounding environment to a display device.

Conventional gas detection systems have been designed to utilize electrochemical sensor devices in conjunction with combined processing and display units. The canister-type sensor devices are arranged as separate units and are connected to the processor/display units by hard-wiring or pin and socket connections. The response of the sensor device is transferred to the processing circuitry, and thereafter a display of appropriate information, such as gas concentration, is generated.

The conventional gas detection systems have as drawbacks the manner in which the sensor devices are interchanged or replaced, and the separate configurations of the processing circuitry and the gas sensor device. In order to change the gas sensor units in the conventional systems, the operator is required to either rewire the sensor device to the processing unit or carefully orient the sensor device so that the pins and sockets align with one another for connection. The lack of self containment of the sensor device and the processing circuitry can tend to be cumbersome to the operator of the system.

It is an object of the present invention to provide a self-contained gas detection apparatus in which both the gas sensor device and the processing circuitry are configured in a common housing.

It is another object of the present invention to provide a gas detection apparatus which enhances the ease in which gas sensors units may be replaced or interchanged by eliminating hard-wire and pin and socket connections.

SUMMARY OF THE INVENTION

The present invention is directed to a gas detection apparatus having a housing defining an inner chamber between a first and a second end, the second end having an access opening to the chamber and an output port disposed at the first end. A microprocessor control circuit is mounted within the chamber and is operable for processing input signals associated with measured gas levels and generating output signals corresponding to same to the output port. The microprocessor circuit includes a first substantially planar conductive interfacing surface. An interchangeable electrochemical sensor device is removably disposed within the chamber via the access opening and is operable for sensing and measuring gas levels and generating the input signals to the microprocessor circuit. The sensor device includes a second substantially planar conductive interfacing surface. An elastomeric connector unit is removably and sealingly disposed between the first and second conductive interfacing surfaces via the access opening and provides a conductive path between the microprocessor circuit and the sensor device for the input signals and electromagnetic shielding therebetween.

DETAILED DESCRIPTION OF THE ILLUSTRATED EMBODIMENTS

Figure 1:
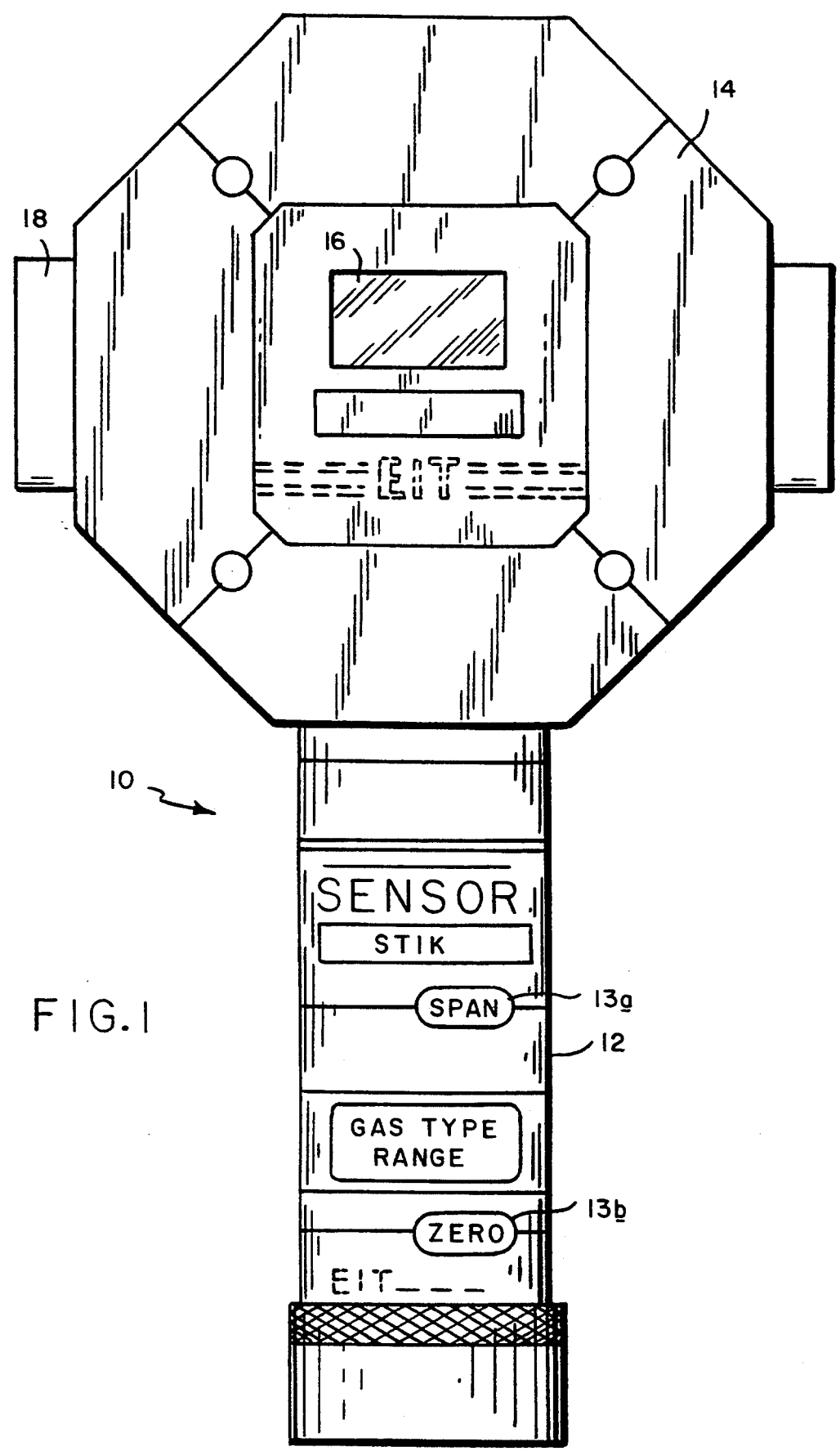
FIG. 1 shows a gas detection apparatus in accordance with the present invention having a gas detection transmitter coupled to a display unit.

With reference now to FIG. 1, a gas detection apparatus 10 in accordance with the present invention is shown. The apparatus 10 includes a gas detection transmitter 12 coupled to a display unit 14. The transmitter 12, as will be further described in detail hereinafter, includes circuitry for sensing gas, and a signal conditioner/amplifier which detects the presence of toxic gas in the air and emits a predetermined industry standard current output which is linearly proportional to the toxic gas concentration in the surrounding environment. The signals generated by the transmitter 12 are provided to the display unit 14. The display unit includes an LCD display 16 for producing digital readouts of the gas concentration with under-range and over-range indicators.

Figure 2:
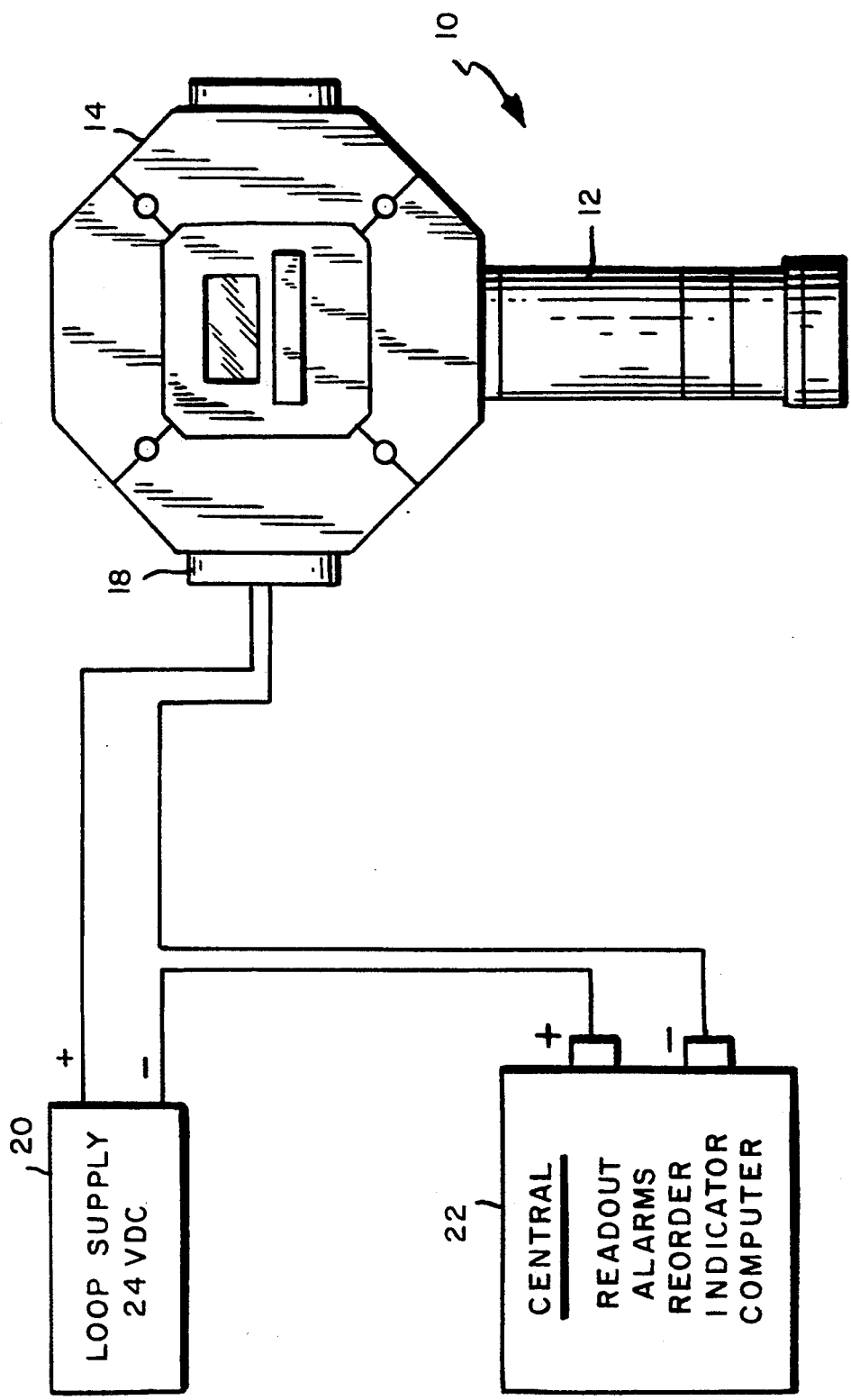
FIG. 2 shows the gas detection apparatus of FIG. 1 coupled to a power supply and a central processing unit.

The gas detection apparatus 10 is configured as a small self-contained unit having an intrinsically safe design for detecting any toxic gas capable of undergoing a chemical reaction. As shown in FIG. 2, the display unit 14 also includes a interfacing port 18 for connection to a loop power supply 20 and central processing unit 22. The central processing unit may comprise a computer with appropriate readouts, alarms, recorders, and indicators.

Figure 3:
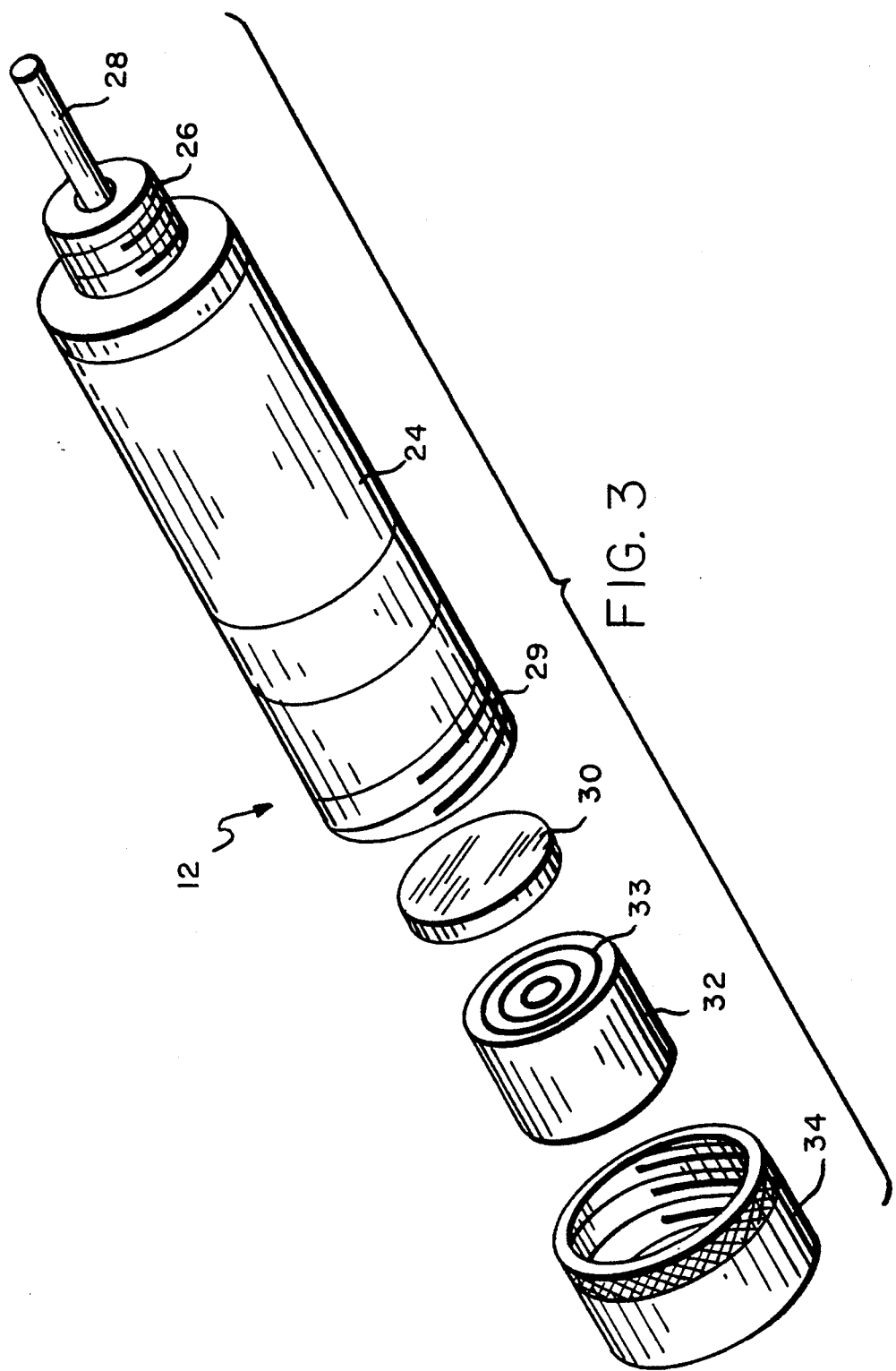
FIG. 3 shows a side perspective view of the gas detection transmitter in a disassembled state.
Figure 4:
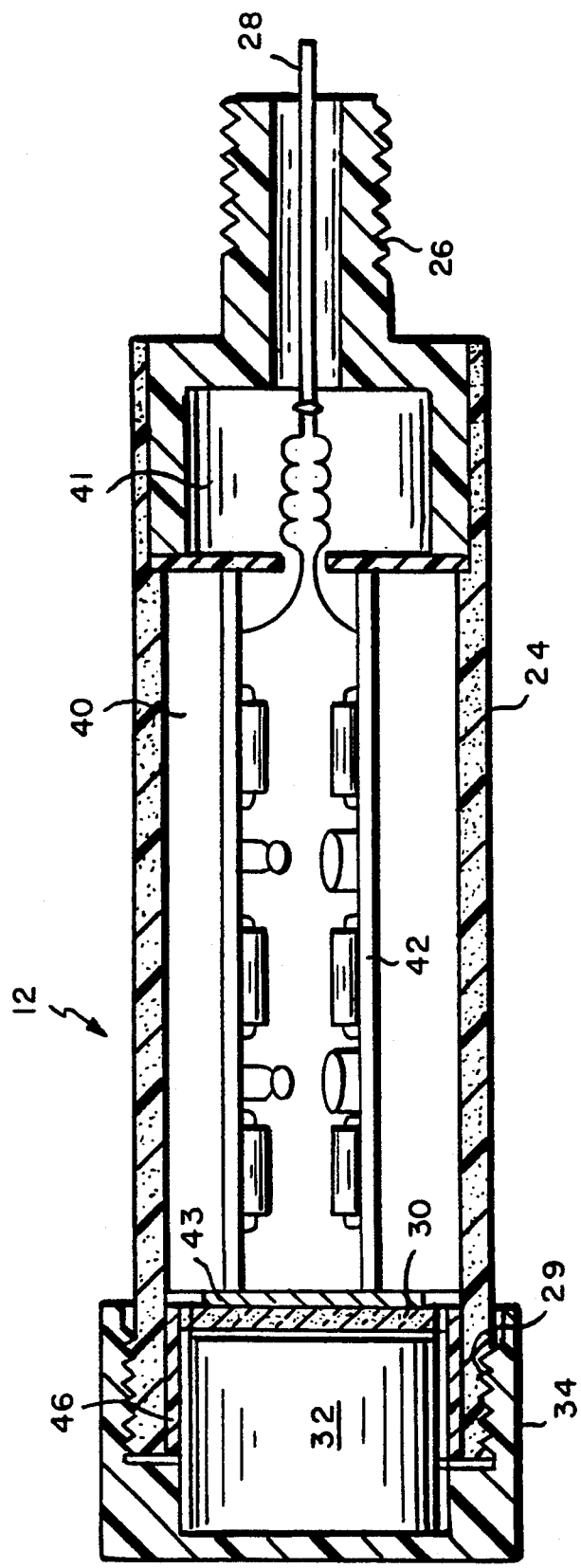
FIG. 4 shows a longitudinal sectional view of the gas detection transmitter.

With reference now to FIGS. 3 and 4, the gas detection transmitter 12 is described in more detail. The transmitter consists of a single unit having a housing 24 which is manufactured from a spun epoxy material, included in which is an impregnated metallic layer allowing rejection of radio frequency or other electromagnetic (RFI-EMI) interferences. The epoxy housing is more resistant to chemical deterioration than ordinary plastic. The circuitry of the transmitter 12 thus resists environmental deterioration caused by moisture, gases, and other adverse contaminants. The epoxy is preferably spun to create the cylindrical shaped housing for the device, but may also be cast to the required shape. With respect to the impregnated layer, any conductive material, such as graphite or nickel, may be used to eliminate the radio frequency interference. Alternatively, the corrosion-resistant outer shell may be impregnated with a matrix of conductive materials to provide this protection.

The housing 24 defines an inner chamber 40 between opposing ends which include a threaded port 26 and an open threaded end 29. Microprocessor control circuitry 42 is mounted within the cavity 40 and includes a two-wire transmitting connection 44 positioned within an RFI cavity 41, and an interface contact pad 43. The microprocessor control circuitry is preferably a two-wire device, operating over an input range of 12-32 VDC in ambient conditions of at least −10° to +50° C. at 10 to 95% RH. The control circuitry operates to output a 4–20 mA signal, linearly proportional to the concentration of gas detected. The circuitry 42 includes an automatic sensor driver, signal conditioner, temperature compensator, and zero and span adjustment means. The zero and calibration operational checks of the apparatus are performed using non-intrusive techniques. For example, a magnetic reed switch is used to calibrate the span adjustment. As a result, there is no need to open the unit for calibration. Touching a magnet to an predetermined indicator areas 13a,13b on the outside of the housing 24, as shown in FIG. 1, effects a simple zero or span adjustment. The mechanical strength and complete environmental protection of the microprocessor control circuitry is enhanced by the mounting within the epoxy housing shell 24.

An electrochemical sensor unit 32 having concentric contact rings 33 is removably positioned within the open threaded end 29 of the housing 24 for contact with the interface pad 43 of the microprocessor control circuitry. The sensor unit 32 is preferably a membrane amperometric electrochemical cell which is a sealed and maintenance-free device. Thus, the sensor requires no replacement of membranes or electrolyte. Sensor 32 is freely interchangeable with other sensors depending on the particular type of toxic gas desired to be detected by the apparatus 10.

In order to provide improved contact between the sensor 32 and the interface contact pad 43 of the microprocessor control circuitry, an elastomeric connector 30 is placed therebetween. The connector 30 serves to seal the chamber as pressure is applied by tightening the end cap 34 onto the threaded end 29. The elastomeric connector is configured to be embedded with a network of fine wires which are exposed when placed under pressure, thus enhancing the contact between the concentric contact rings 33 and the interface contact pad 43. The use of the connector 30 eliminates the need for connecting pins or sockets and greatly simplifies the replacement of the sensor unit 32 in that there is no specific orientation required to replace the sensor unit 32 in connection with the microprocessor control circuitry.

The elastomeric connector 30 additionally provides an environmental seal by preventing moisture and other contaminants from shorting or corroding the connecting area. Also, as the end cap 34 is tightened, the connector tends to rotate causing the exposed wires to rub the connections on both the concentric contact rings 33 and the interface pad 43 so as to keep the connection surfaces clean. The elastomeric connector also serves to provide electromagnetic isolation from surrounding stray interferences.

The end cap serves to secure the sensor unit 30 tightly in place using an o-ring seal. This also prevents the ingress of water and allows efficient operation of the elastomeric connector 30. The end cap may be replaced with a combination range shield/calibration adapter or flow cell. A spacer tube 46 is provided within the open threaded end 29 of the housing 24 to prevent the end cap from over compressing the sensor unit 32 and connector 30.

What is claimed is:

1. A self-contained gas detection apparatus, comprising:
   a housing defining an inner chamber between a first end and a second end, said second end having an access opening to said chamber;
   an output port disposed at said first end;
   a microprocessor control circuit mounted within said chamber and being operable for processing input signals associated with measured gas levels and generating output signals corresponding to same to said output port, said microprocessor control circuit including a first substantially planar conductive interfacing surface;
   an interchangeable electrochemical sensor device removably disposed within said chamber via said access opening and being operable for sensing and measuring gas levels and generating said input signals to said microprocessor control circuit, said sensor device including a second substantially planar conductive interfacing surface; and
   an elastomeric connector unit removably and sealingly disposed between said first and second conductive interfacing surfaces via said access opening, said elastomeric connector unit providing a conductive path between said microprocessor control circuit and said sensor device for said input signals and electromagnetic shielding therebetween.

2. The apparatus of claim 1 further comprising a cap releaseably coupled to said second end of said housing for enclosing and securing said elastomeric connector unit and said sensor device within said chamber.

3. The apparatus of claim 2, wherein said elastomeric connector unit is compressed between said first and second interfacing surfaces as said cap is coupled to said second end.

4. The apparatus of claim 1, wherein said elastomeric connector unit is substantially planar in configuration.

5. The apparatus of claim 1, wherein said elastomeric connector unit comprises a plurality of conductive wires electrically isolated from one another.

6. The apparatus of claim 1, wherein said elastomeric connector unit provides an enhanced conductive interconnection between said first and second as said elastomeric connector unit is compressed therebetween.

7. The apparatus of claim 1, wherein said first and second interfacing surfaces comprise concentric metallic rings.

8. The apparatus of claim 7, wherein said elastomeric connector unit comprises a disc of elastomeric material having a plurality of conductive wires disposed therein.

9. The apparatus of claim 1, wherein said housing comprise a multilayered shell having an impregnated inner lining which provides electromagnetic shielding.

10. The apparatus of claim 1, wherein said output port is coupled to a local display device for transmitting said output signals thereto, said display device being operable for displaying information corresponding to said measured gas levels.

* * * * *